US012657725B2

(12) United States Patent
Sakaguchi

(10) Patent No.: US 12,657,725 B2
(45) Date of Patent: Jun. 16, 2026

(54) INDWELLED STENT LENGTH SIMULATION FOR TREATMENT OF INTRAVASULAR PLAQUE BURDEN

(71) Applicant: TERUMO KABUSHIKI KAISHA, Tokyo (JP)

(72) Inventor: Yuki Sakaguchi, Isehara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 504 days.

(21) Appl. No.: 18/191,974

(22) Filed: Mar. 29, 2023

(65) Prior Publication Data

US 2023/0230252 A1      Jul. 20, 2023

Related U.S. Application Data

(63) Continuation of application No. PCT/JP2021/035259, filed on Sep. 27, 2021.

(30) Foreign Application Priority Data

Sep. 29, 2020      (JP) ................................. 2020-163914

(51) Int. Cl.
  *G06K 9/00*          (2022.01)
  *A61B 6/50*          (2024.01)
          (Continued)

(52) U.S. Cl.
  CPC ................ *G06T 7/11* (2017.01); *A61B 6/504* (2013.01); *G06T 7/0012* (2013.01); *G06T 7/174* (2017.01);
          (Continued)

(58) Field of Classification Search
  CPC ....... A61B 6/504; A61B 8/085; A61B 8/0891; A61B 8/12; A61B 6/032;
          (Continued)

(56) References Cited

U.S. PATENT DOCUMENTS 6,381,350 B1    4/2002 Klingensmith et al.
10,349,919 B2 *  7/2019 Park ....................... A61B 8/488
                (Continued)

FOREIGN PATENT DOCUMENTS

JP        2003503141 A      1/2003
JP        2012176282 A      9/2012
          (Continued)

OTHER PUBLICATIONS

International Search Report (PCT/ISA/210) with translation and Written Opinion (PCT/ISA/237) mailed on Nov. 22, 2021, by the Japanese Patent Office as the International Searching Authority for International Application No. PCT/JP2021/035259. (8 pages).
Extended European Search Report issued on Feb. 28, 2024, in corresponding European Patent Application No. 21875483.6. (8 pages).

*Primary Examiner* — Gregory A Morse
*Assistant Examiner* — Owais I Memon
(74) *Attorney, Agent, or Firm* — .Buchanan Ingersoll & Rooney PC

(57)          ABSTRACT
An information processing device, an information processing method, and a non-transitory computer-readable medium are disclosed. The information processing device includes a processor configured to: acquire transverse tomographic images of a plurality of frames obtained by imaging a blood vessel of a patient, calculate plaque burden at each position of the blood vessel along an axial direction of the blood vessel based on the transverse tomographic images of the plurality of frames, divide a longitudinal cross section of the blood vessel into a first region in which the plaque burden is equal to or greater than a threshold and a second region in which the plaque burden is less than the threshold, and determine, in each of the regions obtained by the division, regions in which both ends of a treatment area of the blood vessel with a predetermined treatment device are to be located.

20 Claims, 17 Drawing Sheets

(51) Int. Cl.

| | | |
|---|---|---|
| *G06T 7/00* | (2017.01) |
| *G06T 7/11* | (2017.01) |
| *G06T 7/174* | (2017.01) |

(52) U.S. Cl.
    CPC ............... *G06T 2207/10072* (2013.01); *G06T 2207/20081* (2013.01); *G06T 2207/30101* (2013.01)

(58) Field of Classification Search
    CPC ....... G06T 2207/30101; G06T 2200/24; G06T 7/11; G06T 7/0012; G06T 7/174; G06T 2207/10072; G06T 2207/20081; G06T 2207/10068; G06T 2207/20076; G06T 2207/20084; G06T 2207/20104; G06T 2207/30096
    See application file for complete search history.

(56) References Cited

U.S. PATENT DOCUMENTS

| | | | |
|---|---|---|---|
| 2012/0253184 A1 | 10/2012 | Furuichi et al. | |
| 2015/0297373 A1* | 10/2015 | Schmitt ..................... | A61F 2/86 623/1.16 |
| 2018/0085170 A1 | 3/2018 | Gopinath | |
| 2020/0294659 A1* | 9/2020 | Gopinath ............. | A61B 5/0066 |
| 2023/0045488 A1* | 2/2023 | Rajguru ............... | A61B 8/0891 |

FOREIGN PATENT DOCUMENTS

| | | |
|---|---|---|
| JP | 2012200532 A | 10/2012 |
| WO | 2017130927 A1 | 8/2017 |

\* cited by examiner

*FIG. 4*

Plaque Burden = XX %

CALCULATION MODEL

51

LUMEN REGION

PLAQUE REGION

*FIG. 14*

PLAQUE REGION

52

IDENTIFICATION MODEL

Plaque Burden = XX %

1

INDWELLED STENT LENGTH SIMULATION FOR TREATMENT OF INTRAVASULAR PLAQUE BURDEN

CROSS-REFERENCES TO RELATED APPLICATIONS

This application is a continuation of International Application No. PCT/JP2021/035259 filed on Sep. 27, 2021, which claims priority to Japanese Application No. 2020-163914 filed on Sep. 29, 2020, the entire content of both of which is incorporated herein by reference.

TECHNOLOGICAL FIELD

The present disclosure generally relates to an information processing device, an information processing method, a program, and a model generation method.

BACKGROUND DISCUSSION

A technology has been used to support diagnostic imaging related to vascular treatment such as percutaneous coronary intervention (PCI). For example, Japanese Patent Application Publication No. 2012-176282 A discloses a medical image processing device for converting three-dimensional computer tomography (CT) data to a two-dimensional projection image, and the medical image processing device extracts a plaque region of a blood vessel from the three-dimensional CT data, calculates a stenosis rate of the blood vessel, and displays a projection image in which a color value of the plaque region is set according to the calculated stenosis rate or the like.

Japanese Patent Application Publication No. 2012-176282 A relates to rule-based extraction of a plaque region from the three-dimensional CT value, and does not always extract a plaque region with high accuracy to calculate a stenosis rate. Japanese Patent Application Publication No. 2012-176282 A further involves three-dimensional CT data and does not calculate a stenosis rate and the like based on two-dimensional data (image).

SUMMARY

An information processing device, an information processing method, a program, and a model generation method are disclosed that are capable of supporting diagnostic imaging related to vascular treatment suitably.

An information processing device according to one aspect includes a processor configured to: acquire transverse tomographic images of a plurality of frames obtained by imaging a blood vessel of a patient, calculate plaque burden at each position of the blood vessel along an axial direction of the blood vessel based on the transverse tomographic images of the plurality of frames, divide a longitudinal cross section of the blood vessel into a first region in which the plaque burden is equal to or greater than a threshold and a second region in which the plaque burden is less than the threshold, and determine, in each of the regions obtained by the division, regions in which both ends of a treatment area of the blood vessel with a predetermined treatment device are to be located.

A non-transitory computer-readable medium storing a program according to another aspect, which when executed by a computer, performs processing comprising: acquiring transverse tomographic images of a plurality of frames obtained by imaging a blood vessel of a patient; calculating plaque burden at each position of the blood vessel along an axial direction of the blood vessel based on the transverse tomographic images of the plurality of frames; dividing a longitudinal cross section of the blood vessel into a first region in which the plaque burden is equal to or greater than a threshold and a second region in which the plaque burden is less than the threshold; and determining, in each of the regions obtained by the division, regions in which both ends of a treatment area of the blood vessel with a predetermined treatment device are to be located.

A model generation method according to a further aspect in which a computer executes processing comprising: acquiring first training data in which data indicating an image region corresponding to plaque is given to a transverse tomographic image obtained by imaging a blood vessel of a patient; generating, based on the first training data, an identification model for identifying the image region corresponding to the plaque in response to the transverse tomographic image inputted; acquiring second training data in which a correct value of plaque burden is given to the transverse tomographic image; and generating, based on a learned parameter obtained by generating the identification model and the second training data, a calculation model for calculating the plaque burden in response to the transverse tomographic image inputted.

According to one aspect, it is possible to suitably support diagnostic imaging related to vascular treatment.

BRIEF DESCRIPTION OF THE DRAWINGS

FIG. 4 is an explanatory diagram related to calculation processing of plaque burden.

FIG. 14 is an explanatory diagram related to calculation processing of plaque burden according to the second embodiment.

DETAILED DESCRIPTION

Set forth below with reference to the accompanying drawings is a detailed description of embodiments of an information processing device, an information processing method, a program, and a model generation method.

First Embodiment

Figure 1:
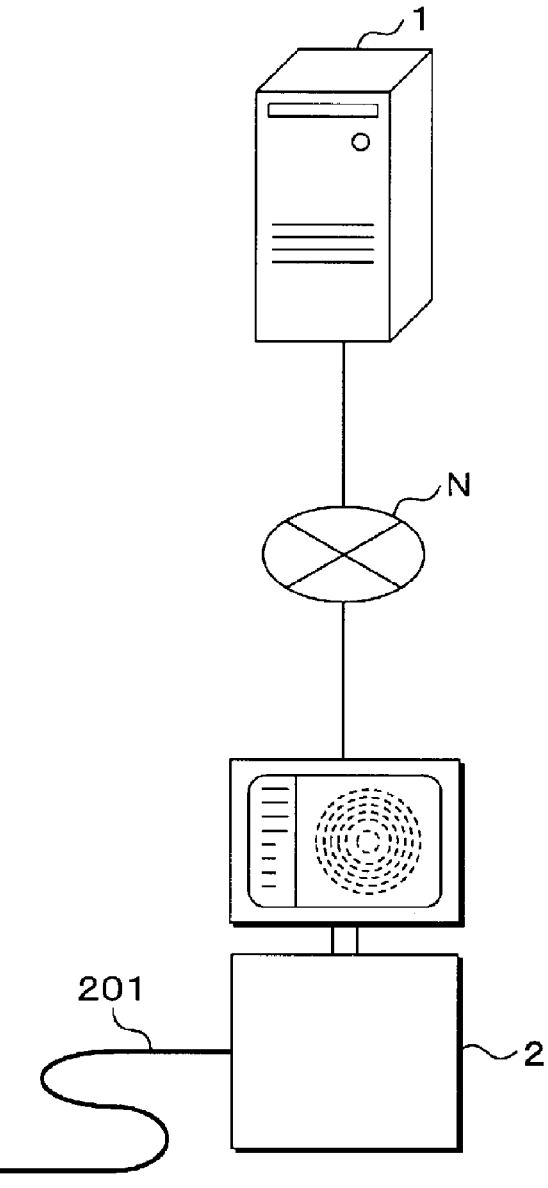
FIG. 1 is an explanatory diagram illustrating a configuration example of a diagnostic imaging system.

FIG. 1 is an explanatory diagram illustrating a configuration example of a diagnostic imaging system. In the present embodiment, description is provided of a diagnostic imaging system that calculates plaque burden based on a transverse tomographic image obtained by imaging a blood vessel of a patient and supports vascular treatment using a predetermined treatment device. A diagnostic imaging system includes a server 1 and the diagnostic imaging device (information processing device) 2. The server 1 and the diagnostic imaging device 2 can be communicably connected via a network N such as the Internet.

The server 1 is a server computer capable of performing various types of information processing and transmitting and receiving information. The server 1 may be, for example, a personal computer. The server 1 performs machine learning to learn predetermined training data, and functions as a generation device that generates a calculation model 51 (see FIG. 4) for calculating plaque burden using a blood vessel tomographic image of a patient as an input.

Figure 4:
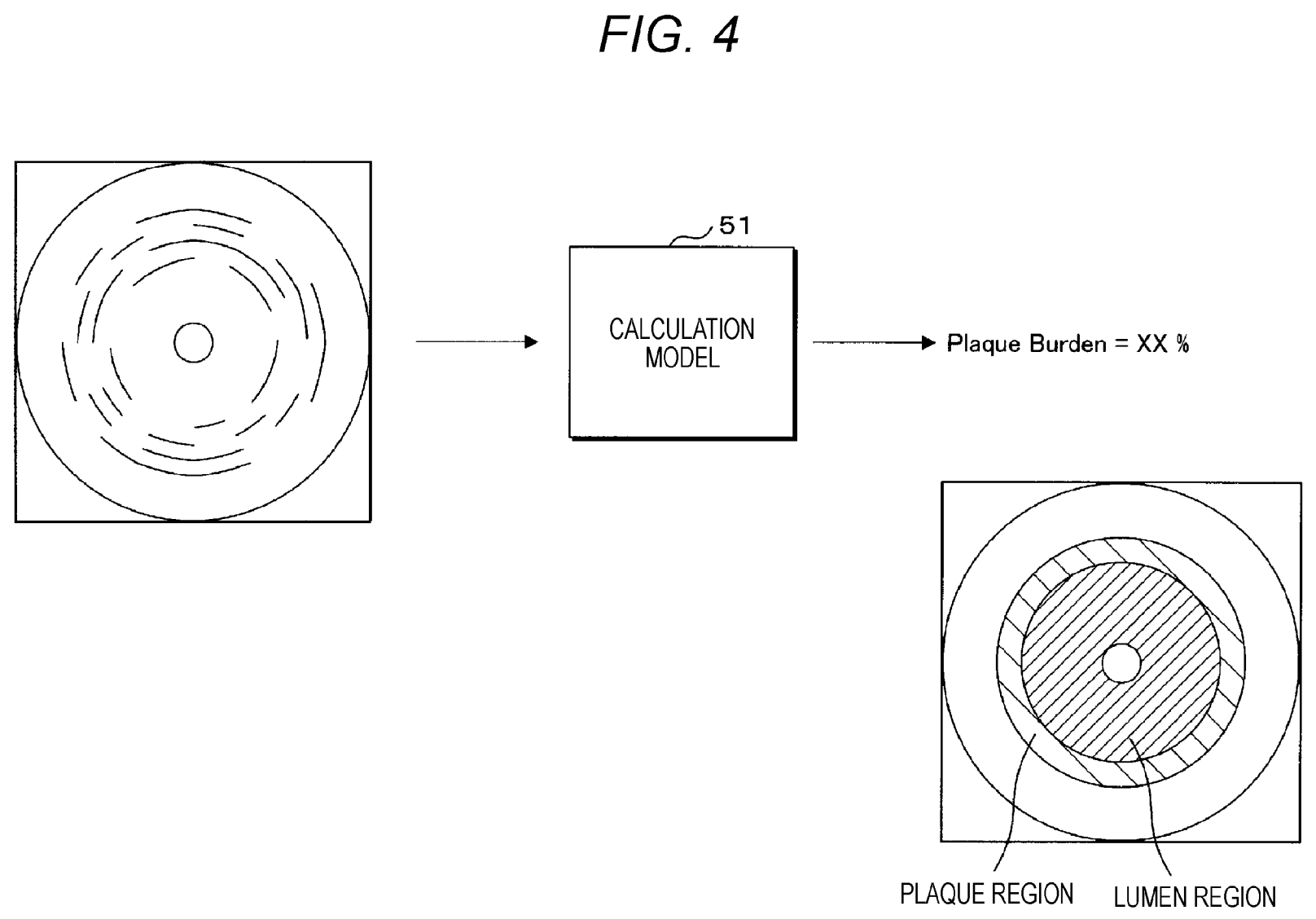

The plaque burden is an area ratio of a plaque to a transverse cross section of a blood vessel, and is a value obtained by dividing cross-sectional areas of the plaque and a tunica media by a blood vessel cross-sectional area (area of a region in external elastic membrane (EEM))(see FIG. 4).

The diagnostic imaging device 2 is an imaging device that captures a medical image obtained by imaging a blood vessel of a patient, and can be, for example, an intravascular ultrasound (IVUS) device that performs an ultrasound examination using a catheter 201. The catheter 201 is a medical instrument inserted into the blood vessel of the patient, and transmits an ultrasound signal from an ultrasound probe attached to a distal end of the catheter 201 and receives a reflected wave. The diagnostic imaging device 2 generates an ultrasound tomographic image based on the reflected wave received by the catheter 201 and displays the ultrasound tomographic image.

In the present embodiment, the diagnostic imaging device 2 is described as an IVUS device, but may be an optical imaging device using optical coherence tomography (OCT) and the like. In addition, the blood vessel tomographic image may be captured by a method other than IVUS or OCT.

Data of the calculation model 51 generated by the server 1 is installed in the diagnostic imaging device 2, and the diagnostic imaging device 2 inputs a blood vessel tomographic image captured using the catheter 201 to the calculation model 51 and calculates plaque burden. The diagnostic imaging device 2 then presents the calculated plaque burden to, for example, a user (medical worker). In addition, the diagnostic imaging device 2 identifies a lesion region of the blood vessel based on the calculated plaque burden, and supports determination of an indwelling position at which a stent (treatment device) to be indwelled in the blood vessel is indwelled.

In the present embodiment, the diagnostic imaging device 2 calculates the plaque burden using the calculation model 51, but the server 1 on a cloud may execute processing using the calculation model 51. Alternatively, for example, a general-purpose computer connected to the diagnostic imaging device 2 may perform the processing. As described above, what executes the series of processes is not particularly limited.

Further, in the present embodiment, a stent is exemplified as the treatment device, but as described later, a balloon for expanding a blood vessel, a rotablator for scraping a stenotic lesion of a blood vessel, or the like may be used.

Figure 2:
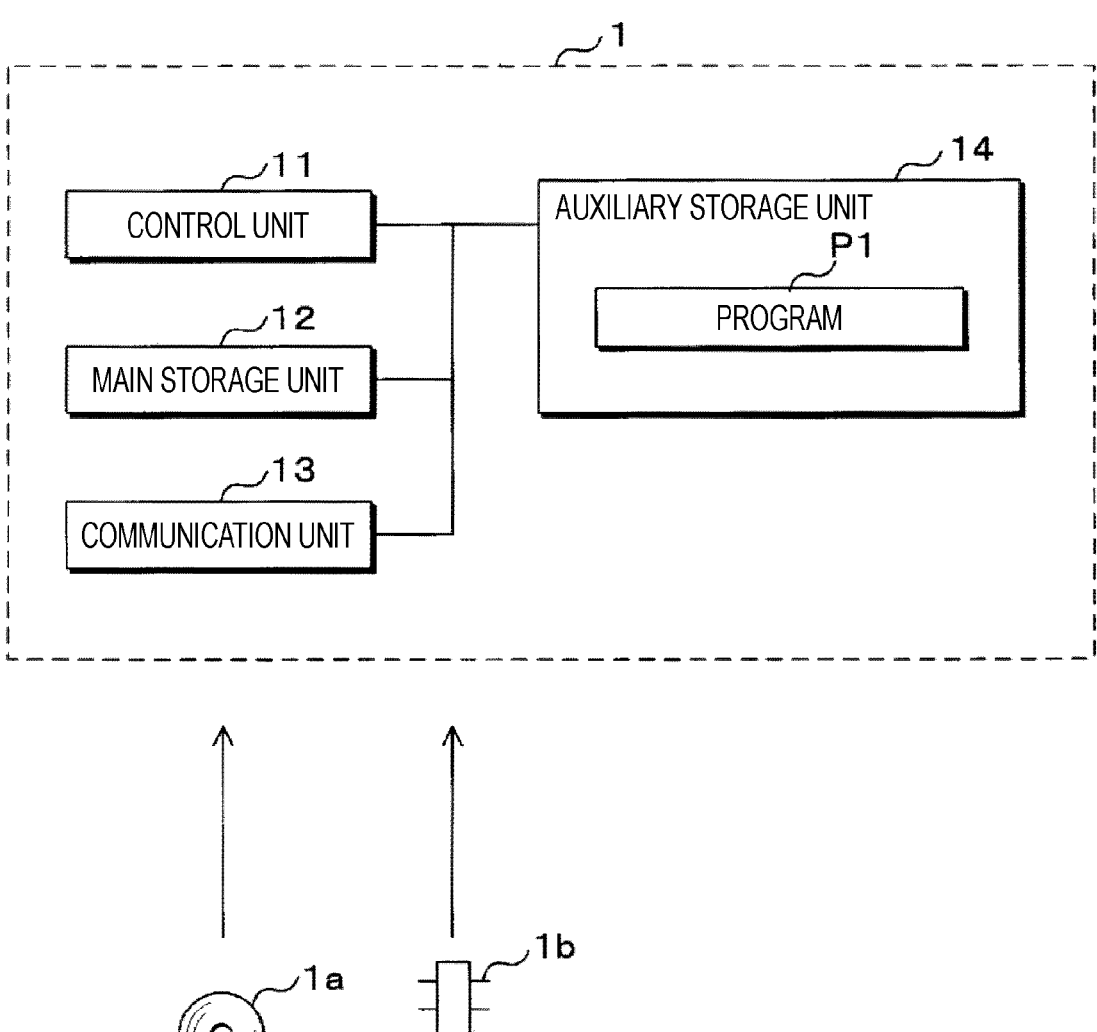
FIG. 2 is a block diagram illustrating a configuration example of a server.

FIG. 2 is a block diagram illustrating a configuration example of the server 1. The server 1 can include a control unit 11, a main storage unit 12, a communication unit 13, and an auxiliary storage unit 14.

The control unit 11 includes one or a plurality of arithmetic processing devices such as a central processing unit (CPU), a micro-processing unit (MPU), and a graphics processing unit (GPU), and performs various types of information processing, control processing, and the like by reading and executing a program P1 stored in the auxiliary storage unit 14. The main storage unit 12 can be a temporary storage area such as a static random access memory (SRAM), a dynamic random access memory (DRAM), or a flash memory, and temporarily stores data necessary for the control unit 11 to execute arithmetic processing. The communication unit 13 is a communication module for performing processing related to communication, and transmits and receives information to and from an external device. The auxiliary storage unit 14 is a non-volatile storage area such as a large-capacity memory or a hard disk, and stores the program P1 necessary for the control unit 11 to execute processing and other data.

The server 1 may be a multi-computer including a plurality of computers, or may be a virtual machine virtually configured by software.

Further, in the present embodiment, the server 1 is not limited to have the above configuration, and may include, for example, an input unit that receives an operation input, a display unit that displays an image, and the like. Further, the server 1 may include a reading unit that reads a portable storage medium 1*a* such as a compact disk (CD)-ROM and a digital versatile disc (DVD)-ROM, and may read the program P1 from the portable storage medium 1*a* to execute the program P1. Alternatively, the server 1 may read the program P1 from a semiconductor memory 1*b*.

Figure 3:
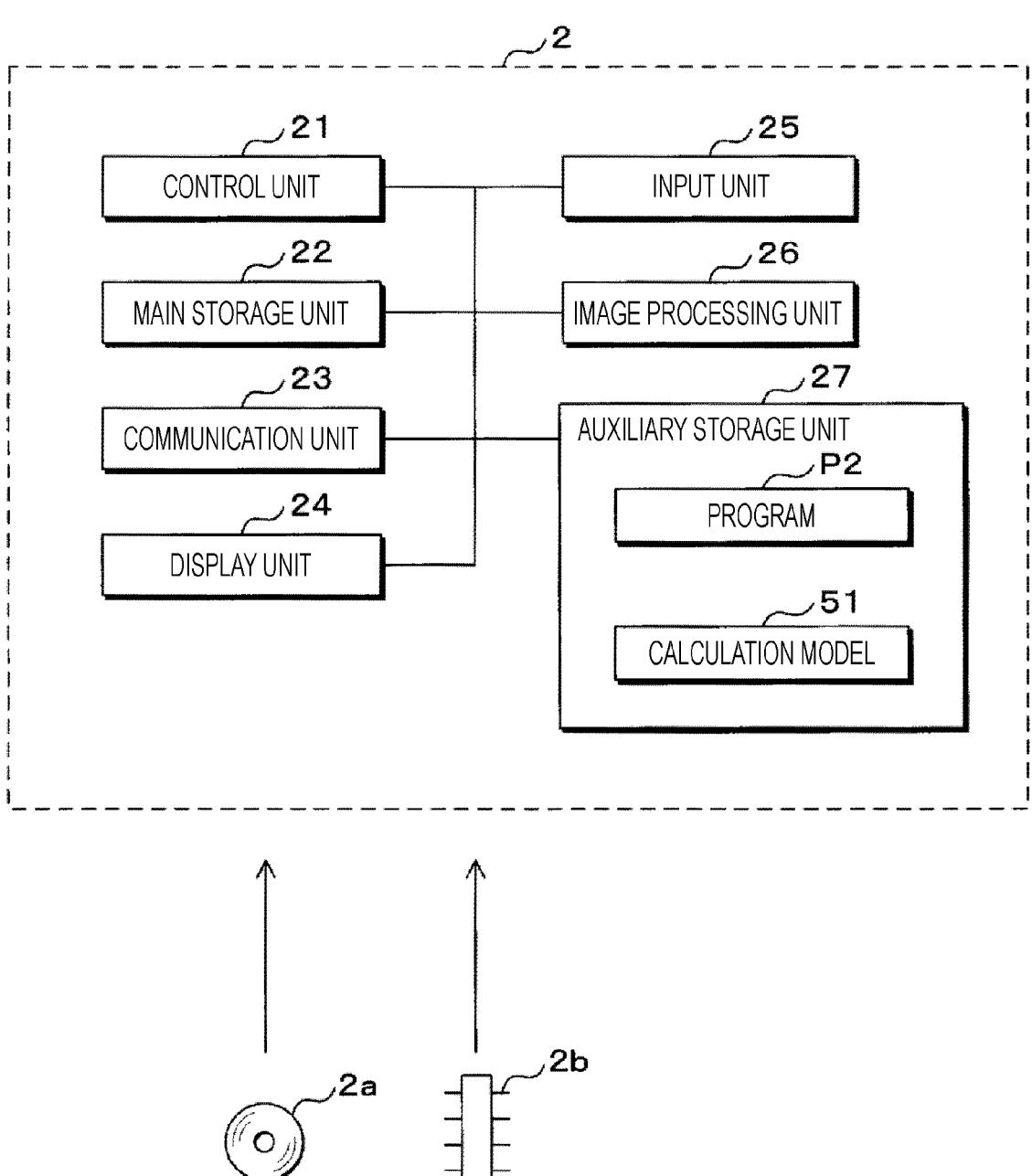
FIG. 3 is a block diagram illustrating a configuration example of a diagnostic imaging device.

FIG. 3 is a block diagram illustrating a configuration example of the diagnostic imaging device 2. The diagnostic imaging device 2 includes a control unit 21, a main storage unit 22, a communication unit 23, a display unit 24, an input unit 25, an image processing unit 26, and an auxiliary storage unit 27.

The control unit 21 is an arithmetic processing device such as one or a plurality of CPUs, MPUs, and GPUs, and performs various types of information processing, control processing, and the like by reading and executing a program P2 stored in the auxiliary storage unit 27. The main storage unit 22 is a temporary storage area such as a RAM, and temporarily stores data necessary for the control unit 21 to execute arithmetic processing. The communication unit 23 is a communication module for performing processing related to communication, and transmits and receives information to and from an external device. The display unit 24 is a display screen such as a liquid crystal display, and displays an image. The input unit 25 is an operation interface such as a keyboard and a mouse, and receives an operation input from the user. The image processing unit 26 is an image processing module that processes signals transmitted and received via the catheter 201 and generates a tomographic image.

The auxiliary storage unit 27 is a non-volatile storage area such as a hard disk or a large-capacity memory, and stores the program P2 necessary for the control unit 21 to execute processing and other data. The auxiliary storage unit 27 also stores the calculation model 51. The calculation model 51 is a machine learning model generated by learning predetermined training data, and is a learned model that calculates plaque burden using, as an input, a transverse tomographic image of a blood vessel captured by the diagnostic imaging device 2. The calculation model 51 is assumed to be used as a program module constituting a part of artificial intelligence software.

The diagnostic imaging device 2 may include a reading unit that reads a portable storage medium 2a such as a CD-ROM, and may read the program P2 from the portable storage medium 2a to execute the program P2. Alternatively, the diagnostic imaging device 2 may read the program P2 from a semiconductor memory 2b.

FIG. 4 is an explanatory diagram related to calculation processing of plaque burden. FIG. 4 illustrates a state in which each frame of a blood vessel tomographic image captured by the diagnostic imaging device 2 is input to the calculation model 51 to calculate plaque burden.

The calculation model 51 is a machine learning model that has learned predetermined training data, and can be, for example, a convolution neural network (CNN). The calculation model 51 only needs to be a model capable of calculating plaque burden from the blood vessel tomographic image, and may be a model based on another learning algorithm such as a neural network other than CNN, a decision tree, or a support vector machine (SVM).

The calculation model 51 includes an input layer that receives an input of an image (tomographic image), an intermediate layer that extracts a feature amount of an input image, and an output layer that calculates (outputs) plaque burden. The input layer receives an input of an image and transfers data on the input image to the intermediate layer. The intermediate layer includes a convolutional layer that convolves data on the input image, extracts a feature amount of the input image, and transfers the feature amount to the output layer. The output layer calculates the plaque burden based on the feature amount extracted in the intermediate layer.

In the present embodiment, the processing executed by the calculation model 51 is treated as a regression problem, and the plaque burden is predicted with continuous values. This processing may be treated as a classification problem, and the plaque burden may be predicted (classified) within a certain numerical range, for example, "0 to X1", "X1 to X2", "X2 to X3", (0<X1<X2<X3 . . . ). Alternatively, the plaque burden may be classified into a plurality of stages (classified into, for example, red zone, orange zone, yellow zone, . . . , and so on) without numerically predicting the plaque burden.

The server 1 generates the calculation model 51 by using, as training data (second training data), data in which a correct value of the plaque burden is given to a blood vessel tomographic image (transverse tomographic image) for training. The tomographic image for training is a blood vessel tomographic image captured with an actual patient as the subject, and the correct value is an actual value of plaque burden in the tomographic image of the patient. The server 1 inputs the tomographic image for training to the calculation model 51 to calculate the plaque burden, and compares the plaque burden with the correct value. The server 1 optimizes parameters such as weights between neurons so that the two approximate to each other, and generates the calculation model 51.

The diagnostic imaging device 2 uses the calculation model 51 generated by the server 1 to calculate plaque burden in a blood vessel of a patient who undergoes catheter treatment. Specifically, the diagnostic imaging device 2 sequentially inputs, to the calculation model 51, tomographic images of a plurality of frames captured according to pull-back operation of the catheter 201, and calculates the plaque burden in each frame. As a result, the diagnostic imaging device 2 calculates an area ratio obtained by dividing an area of an image region (referred to as "plaque region" in the following description) corresponding to the plaque and the tunica media by an area of an EEM region (region obtained by adding a lumen region to the plaque region), that is, plaque burden (see the lower right of FIG. 4).

The diagnostic imaging device 2 presents, to the user, the plaque burden in each frame calculated above, that is, the plaque burden at each position of the blood vessel along the axial direction, and supports determination of a position at which the stent is indwelled.

Figure 5:
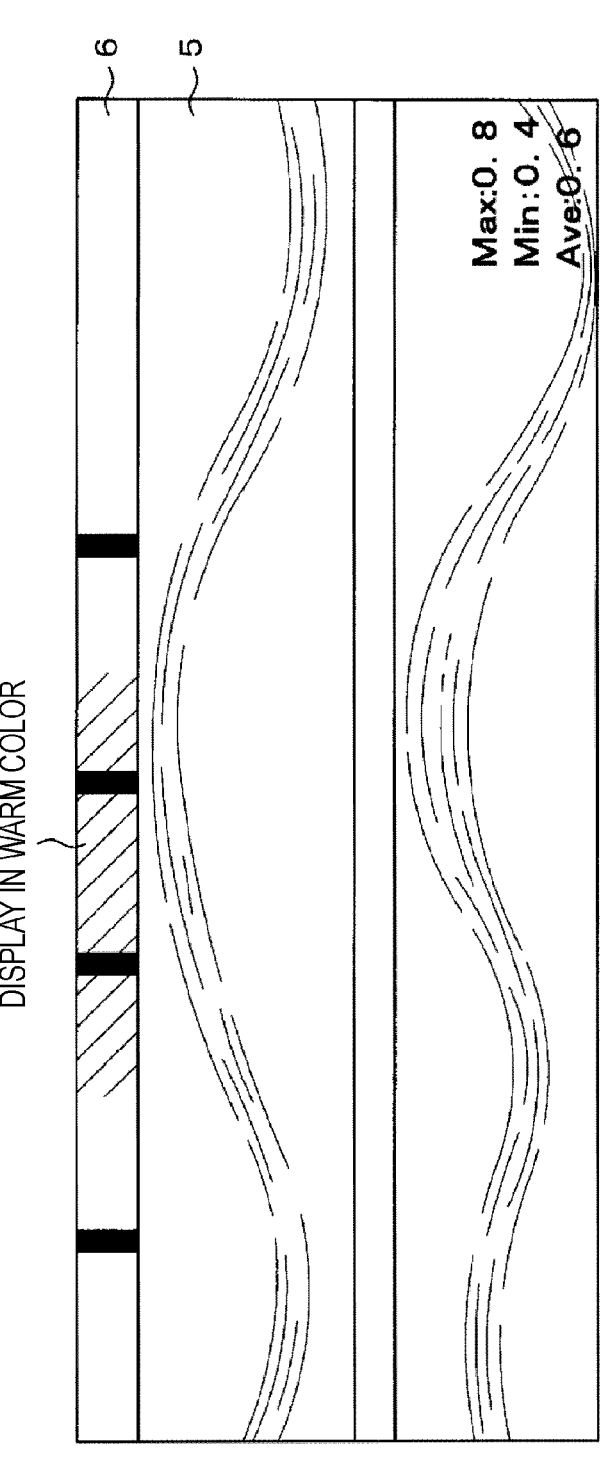
FIG. 5 is an explanatory diagram illustrating a display example of plaque burden.

FIG. 5 is an explanatory diagram illustrating a display example of the plaque burden. In the present embodiment, the diagnostic imaging device 2 displays a predetermined object (first object) representing the magnitude of the plaque burden at each position of the blood vessel, corresponding to a longitudinal tomographic image 5 obtained by reconstructing the transverse tomographic images of a plurality of frames. Specifically, as illustrated in FIG. 5, the diagnostic imaging device 2 displays a gradation bar 6 in which a display color is gradually changed according to the magnitude of the plaque burden on the upper side of the longitudinal tomographic image 5.

The longitudinal tomographic image 5 is a longitudinal cross section in which the state of the blood vessel is reproduced along the axial direction (flow direction) of the blood vessel, and is generated from the transverse tomographic images of a plurality of frames captured according to the pull-back operation. For example, as illustrated in FIG. 5, the diagnostic imaging device 2 displays the longitudinal tomographic image 5 with the axial direction of the blood vessel as the transverse direction.

The diagnostic imaging device 2 displays, on the upper side of the longitudinal tomographic image 5, the gradation bar 6 having substantially the same length as the length of the longitudinal tomographic image 5 along the axial direction. The gradation bar 6 can be a rod-like object representing the magnitude of the plaque burden, and can be a display bar in which the display color is changed depending on each position of the corresponding longitudinal tomographic image 5, that is, the magnitude of the plaque burden in the transverse tomographic image of each frame. The diagnostic imaging device 2 changes the display color at each position of the gradation bar 6, according to the magnitude of the plaque burden at each position on the longitudinal tomographic image 5.

In FIG. 5, for convenience, a region having large plaque burden (region equal to or greater than a threshold) is shown with hatching. As described below, the gradation of the display color in the gradation bar 6 can be finely set according to the numerical value of the plaque burden, but in FIG. 5, for convenience, a region having large plaque burden is shown with the same hatching.

In the present embodiment, the description is given assuming that the object indicating the magnitude of plaque burden is the gradation bar 6, but the object is not limited to the gradation bar 6. For example, the diagnostic imaging device 2 may display a line graph indicating the magnitude of plaque burden on the upper side of the longitudinal tomographic image 5. As described above, the gradation bar 6 is an example of the object, and any object may be used as long as the object appropriately indicates the magnitude of plaque burden.

For example, the diagnostic imaging device 2 refers to a predetermined threshold (for example, 50%) set by default, and sets a display color for a region having many plaques. Specifically, the diagnostic imaging device 2 sets the display color for a region having plaque burden equal to or greater than the threshold to a warm color (orange, for example), and sets the display color for a region having plaque burden less than the threshold to a default color (white, for example). The diagnostic imaging device 2 then changes the display color (for example, increases the lightness) so that the larger the plaque burden, the more the region having plaque burden equal to or greater than the threshold is emphasized, and performs gradation display.

As a method of gradation display, for example, it is assumed that lightness is changed, but hue, saturation, and the like may be changed, and a specific display method is not particularly limited.

In a case where the gradation bar 6 is displayed as described above, it is preferable that the diagnostic imaging device 2 hides a region in which the reliability of the calculation result of the plaque burden in the calculation model 51 is relatively low (hereinafter, referred to as a "low reliability region"). In FIG. 5, the low reliability region is illustrated in black. For the calculation of the plaque burden in each frame using the calculation model 51, the diagnostic imaging device 2 acquires the reliability of the calculated value (for example, a probability value of 0 to 1) from the calculation model 51 together with the plaque burden in each frame. In a case where the reliability at each position (frame) of the blood vessel is equal to or less than a predetermined value, that is, in a case where the reliability is relatively low, the diagnostic imaging device 2 leaves a region on the corresponding gradation bar 6 blank as the low reliability region. As a result, the certainty of the calculation result of the plaque burden can be presented to the user.

As described above, the diagnostic imaging device 2 displays the gradation bar 6 together with the longitudinal tomographic image 5, and quantitatively presents the state of the blood vessel at each position. As illustrated in FIG. 5, the diagnostic imaging device 2 can display a maximum value, a minimum value, and an average value of the plaque burden, which helps enable the user (for example, a medical worker) to grasp the state of the blood vessel and determine a treatment area to be treated with a treatment device such as a stent.

Figure 6:
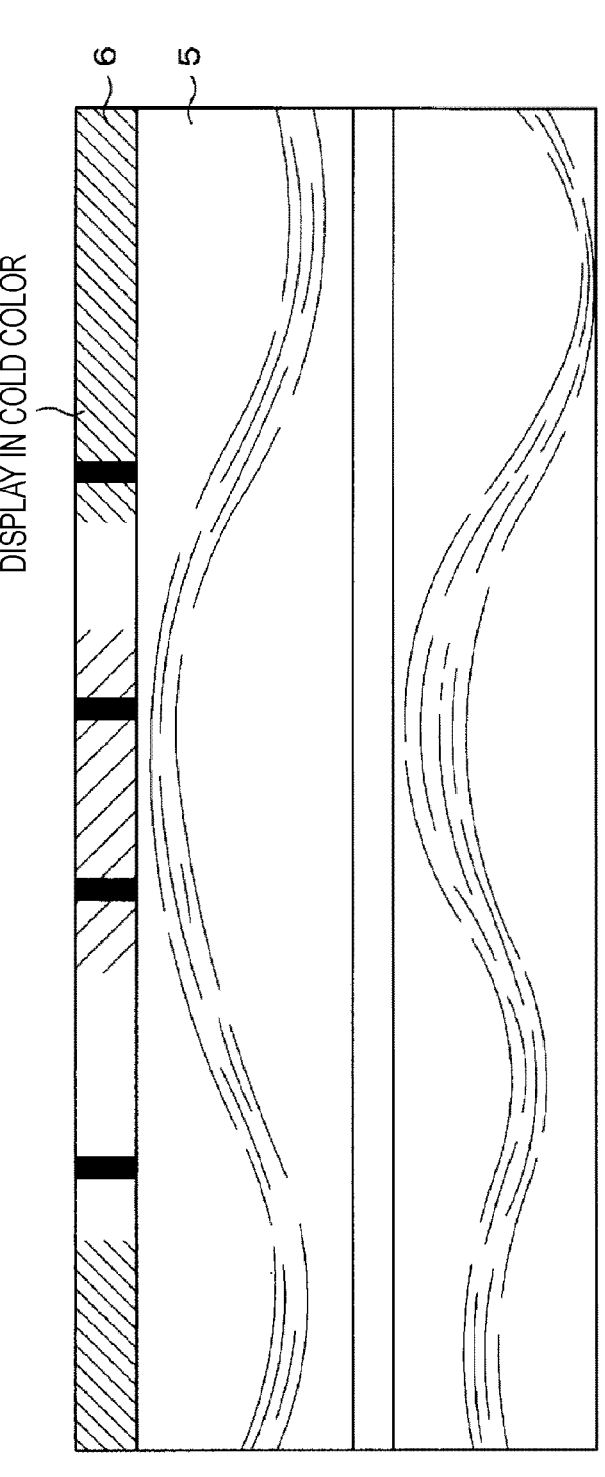
FIG. 6 is an explanatory diagram illustrating another display example of plaque burden.

FIG. 6 is an explanatory diagram illustrating another display example of the plaque burden. In FIG. 5, the display example has been described in which the warm color is displayed for the region having the plaque burden equal to or greater than the threshold, but gradation display may be performed also for the region having the plaque burden less than the threshold, that is, the region having few plaques.

For example, the diagnostic imaging device 2 sets the display color for the region having the plaque burden equal to or greater than the threshold to a warm color, and sets the display color for the region having the plaque burden less than the threshold to a cold color. In FIG. 6, the region having the plaque burden equal to or greater than the threshold and the region having the plaque burden less than the threshold are shown with different hatching. Similarly to the region having the plaque burden equal to or greater than the threshold, the diagnostic imaging device 2 changes the display color (for example, increases the lightness) as the plaque burden is smaller, and performs gradation display. As described above, the diagnostic imaging device 2 may present a region that has a large number of plaques and needs to be treated, and may also present a region that has a small number of plaques and has a relatively low need for treatment.

In the example of FIG. 6, the number of regions for gradation display is two, but it is possible that a threshold is further provided and gradation display is performed in three or more regions.

In addition, in a case where the gradation display is performed, the user may set a threshold as a display reference. Specifically, the diagnostic imaging device 2 receives, from the user, a setting input for changing the threshold from a default value to an another value (for example, a threshold based on user preference), determines the region having the plaque burden equal to or greater than the threshold and the region having the plaque burden less than the threshold according to the set threshold, and changes the display color, which helps enable the user to visualize a region of interest by himself/herself, resulting in supporting the user more suitably.

Figure 7:
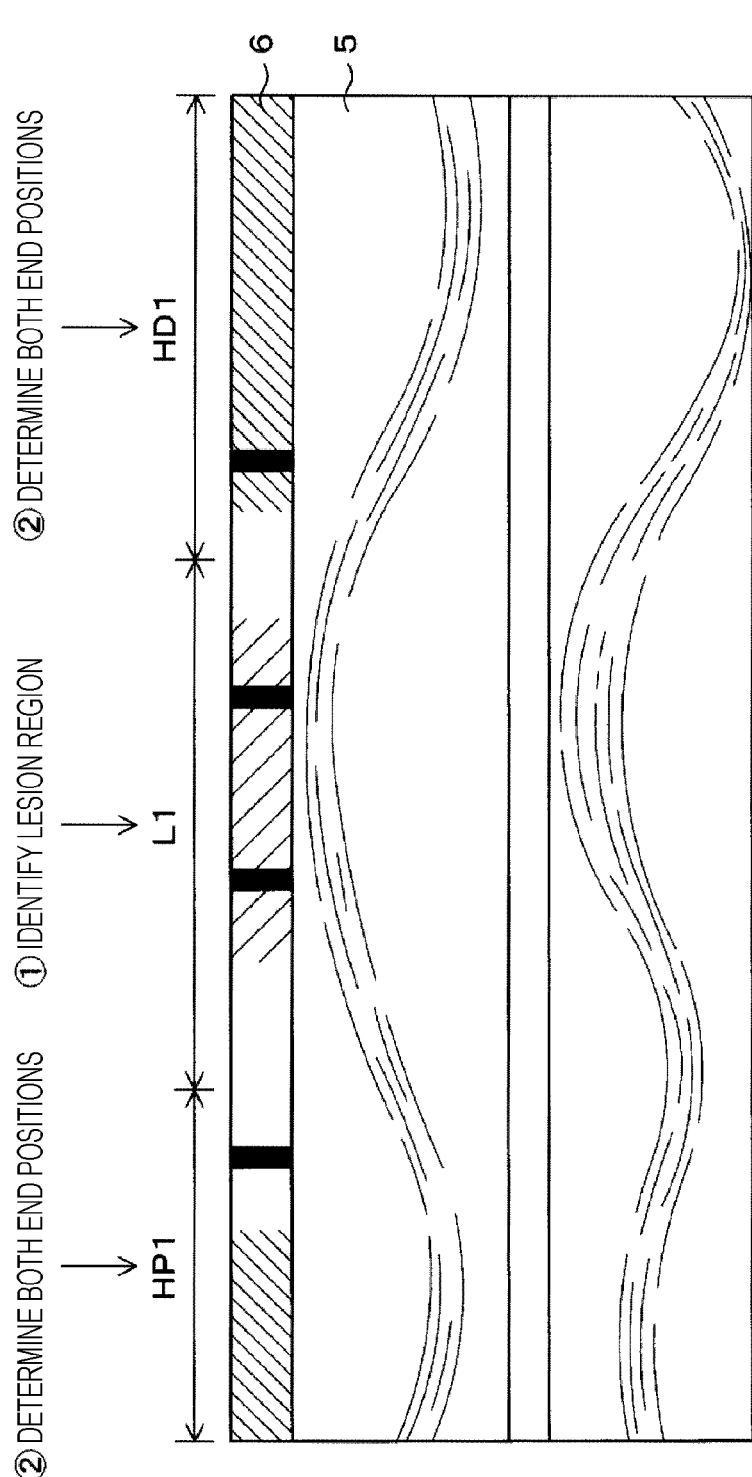
FIG. 7 is an explanatory diagram related to determination processing of a treatment area of a blood vessel.

FIG. 7 is an explanatory diagram related to determination processing of a treatment area of a blood vessel. In the present embodiment, a treatment area to be treated with a predetermined treatment device is further presented to the user based on the calculation result of the plaque burden.

Specifically, the diagnostic imaging device 2 determines positions of both ends of a stent indwelled in the blood vessel. In the case of vascular treatment such as PCI, it can be preferable to indwell the stent so as to cover the entire lesion, however in practice, it can be difficult to cover the entire lesion because plaques are continuously present. For example, the stent can be indwelled so that both ends of the stent are located in a normal site where no plaque is present; however, when it is difficult to do so, the stent is indwelled so that both ends of the stent are located at a site where the plaque burden is a predetermined value (for example, 50%) or less. If that is also difficult, the stent can be indwelled so that both ends of the stent are located at a site with the least plaque burden.

At present, the plaque burden of all frames is not calculated as described above, and a stenosed site is visually identified on the image, and the plaque burden of several frames is measured as necessary. In view of this, in the present embodiment, an area where both ends of the stent should be located is determined based on the plaque burden calculated by the calculation model 51.

In the present embodiment, the stent is exemplified as a treatment device, but the treatment device is not limited to the stent. For example, the diagnostic imaging device 2 may determine both end positions of an expansion area to be expanded with a balloon used for expanding a blood vessel. Alternatively, for example, the diagnostic imaging device 2 may determine both end positions of a cut area to be cut by a rotablator used for scraping a hard lesion (for example, calcified tissue). As described above, the diagnostic imaging device 2 only needs to be able to determine both end positions of a treatment area to be treated with a treatment device inserted into a blood vessel, and the treatment device is not limited to the stent.

First, the diagnostic imaging device 2 divides the longitudinal tomographic image 5 (longitudinal cross section) of the blood vessel into a first region in which the plaque burden is equal to or greater than a predetermined threshold and a second region in which the plaque burden is less than the threshold. The threshold can be, for example, the same value as the threshold used as the reference for the gradation display described above, but may be a different value. The diagnostic imaging device 2 divides, based on the plaque burden in each frame calculated by the calculation model 51, the longitudinal tomographic image 5 into first regions L1, L2, L3 (L: Lesion) in which the plaque burden is equal to or greater than the threshold and second regions H1, H2, H3 (H: Healthy) in which the plaque burden is less than the threshold.

In the present embodiment, the diagnostic imaging device 2 identifies the first regions LX (X=1, 2, 3 . . . ) including the position (frame) where the plaque burden takes the maximum value as a lesion region LX in which the stent is to be indwelled. The diagnostic imaging device 2 then determines two second regions HY and HZ (Y, Z=1, 2, 3 . . . ) located on both sides of the identified lesion region LX as regions where both ends of the stent should be located.

FIG. 7 illustrates the longitudinal tomographic image 5 in which one first region L1 and two second regions HP1 and HD1 (P: Proximal, D: Distal) are present. In a case where the plaque burden takes the maximum value in the first region L1, the diagnostic imaging device 2 determines the second regions HP1 and HD1 sandwiching the first region L1 between the second regions HP1 and HD1 as the regions where both ends of the stent should be located.

For example, in a case where there is a low reliability region in which the reliability of the calculation result of the plaque burden is relatively low, it is preferable that the diagnostic imaging device 2 groups a plurality of the first regions or the second regions extending over the low reliability region as the same region. For example, in FIG. 7, two low reliability regions are present in the first region L1. In this case, the diagnostic imaging device 2 determines whether or not the length of each low reliability region in the axial direction of the blood vessel is equal to or less than a predetermined length (for example, 1 mm). In a case where the length of the low reliability region is equal to or less than the predetermined length, the diagnostic imaging device 2 treats the plurality of first regions extending over the low reliability region as the same region and divides the regions. In the example of FIG. 7, since the length of both of the two low reliability regions is equal to or less than the predetermined length, the diagnostic imaging device 2 divides the three regions extending over the low reliability region into the same first region L1.

Similarly for the second region, in a case where there is a plurality of second regions extending over the low reliability region of which the length is equal to or less than the predetermined length, the diagnostic imaging device 2 divides the plurality of second regions as the same region. As described above, in a case where the length of the low reliability region in the axial direction is equal to or less than the predetermined length, the diagnostic imaging device 2 divides the plurality of first regions or the plurality of second regions extending over the low reliability region as the same region. As a result, the indwelling position of the stent can be suitably determined while reliability can be ensured.

In addition, the user may change the predetermined length. For example, the diagnostic imaging device 2 receives a setting input for changing a default value of the predetermined length to a value (for example, lengths in predetermined increments of 0.6 mm, 0.8 mm, 1.2 mm, . . . ). The diagnostic imaging device 2 divides each region by determining whether the length is equal to or less than a set predetermined length, which helps enable the user to determine the indwelling position of the stent more suitably.

Similarly to the gradation display, in the diagnostic imaging device 2, the user may change a threshold serving as a reference for the region division. In this case, the diagnostic imaging device 2 may be able to set different thresholds for the proximal side (Proximal) and the distal side (Distal) of the blood vessel. For example, in a case where 50% is set as the threshold on the proximal side and 60% is set as the threshold on the distal side, the diagnostic imaging device 2 performs division with a position where the plaque burden is equal to or greater than 50% as viewed from the left side of FIG. 7 used as the start point of the first region and a position where the plaque burden is less than 60% used as the end point of the first region, which helps enable the user to finely adjust the first region and the second region by himself/herself.

Figure 8:
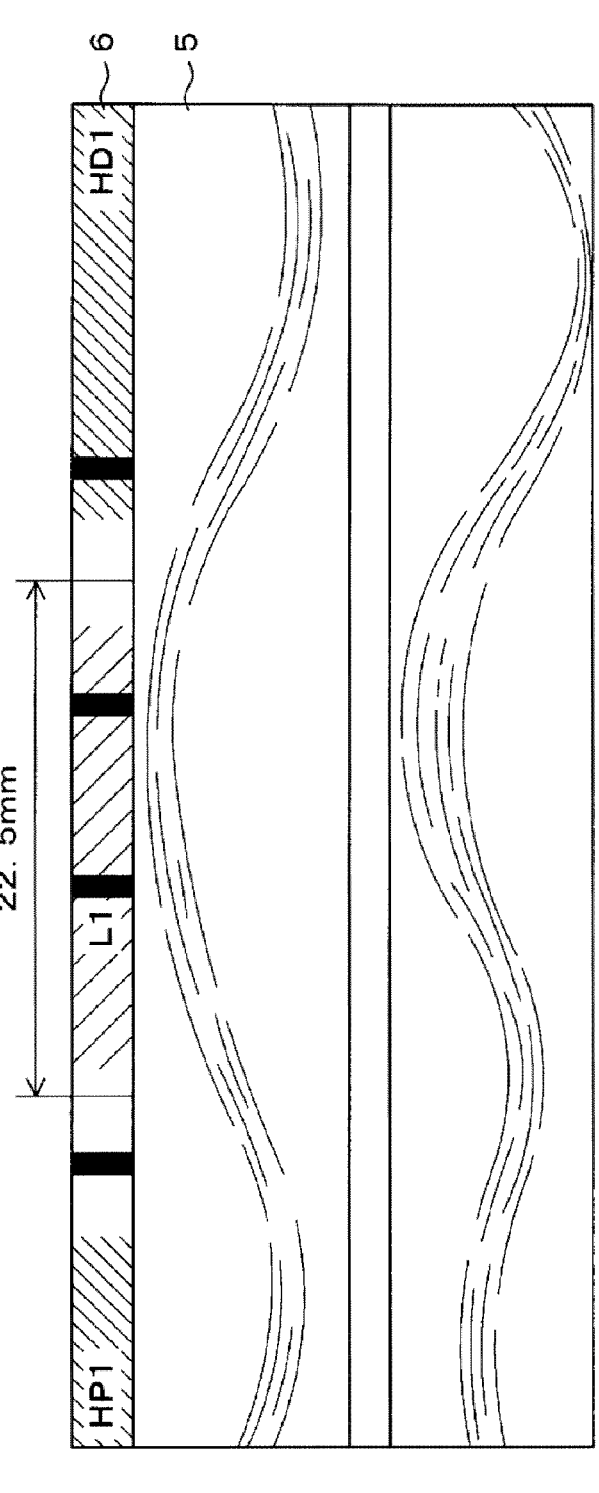
FIG. 8 is an explanatory diagram illustrating a display example of a lesion length.

FIG. 8 is an explanatory diagram illustrating a display example of a lesion length. As described above, the diagnostic imaging device 2 divides the longitudinal tomographic image 5 into the first regions L1, L2, L3 . . . and the second regions H1, H2, H3 . . . , and identifies a lesion region L1. In a case where the lesion region L1 is identified, the diagnostic imaging device 2 measures the length of the lesion region L1 in the axial direction of the blood vessel, that is, the lesion length, and displays the length in association with the lesion region L1 in the longitudinal tomographic image 5. Specifically, as illustrated in FIG. 8, the diagnostic imaging device 2 displays a portion corresponding to the lesion region L1 on the gradation bar 6 with an arrow, and displays the lesion length. Thereby, the length of a lesion site can be visualized.

Figure 9:
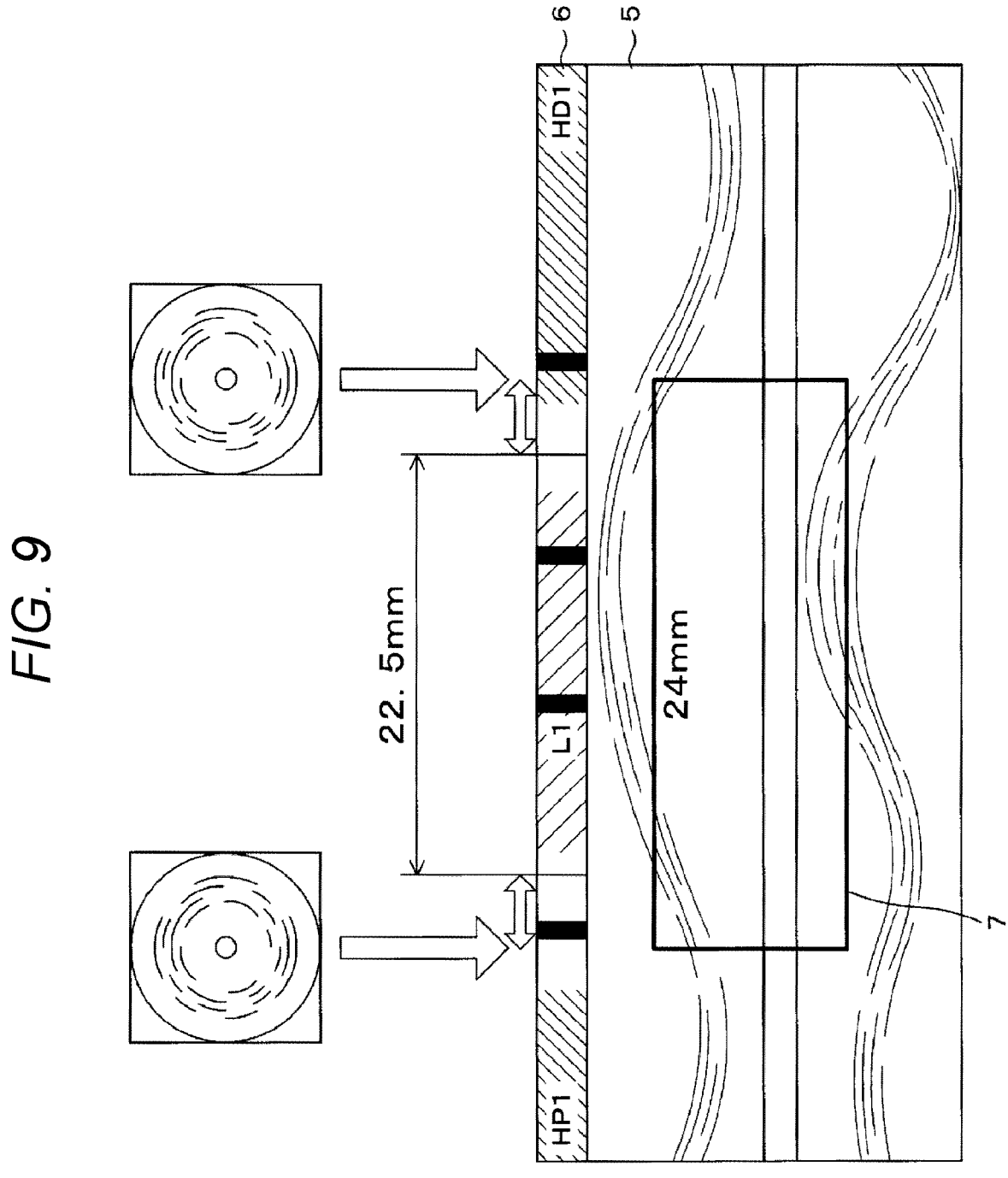
FIG. 9 is an explanatory diagram illustrating an example where a stent is superimposed.

FIG. 9 is an explanatory diagram illustrating an example where a stent is superimposed. In the present embodiment, the diagnostic imaging device 2 further presents, to the user, a treatment area to be treated with the treatment device, that is, an area in which the stent is to be indwelled. Specifically, the diagnostic imaging device 2 superimposes and displays a stent region 7 (second object) representing the size of the stent (treatment device) on the longitudinal tomographic image 5.

The stent region 7 can be an object simulating the stent indwelled in the blood vessel, and can be, for example, a rectangular object representing an area in which the stent is indwelled. It is only required that at least the length of the stent region 7 in the axial direction is equal to the actual length of the stent, and the length of the stent region 7 in the radial direction (length in the longitudinal direction in FIG. 8) is not required to be equal to the actual length of the stent.

Further, in the present embodiment, since the treatment device is a stent, the shape of the object is a rectangular shape; however, for example, in a case where the treatment device is a balloon, the shape of the object may be a sandbag shape (i.e., a generally rectangular shape having an increased diameter in a central portion of the object). As described above, the diagnostic imaging device 2 only needs to be able to display an object having a shape corresponding to the treatment device.

For example, the diagnostic imaging device 2 displays the stent region 7 having a length equal to or longer than the lesion length measured above such that both ends of the stent region 7 are located in the second regions HP1 and HD1 determined as the regions where both ends should be located. For example, the diagnostic imaging device 2 stores, in the auxiliary storage unit 27, information on stent products in predetermined length increments (for example, 9 mm, 12 mm, 15 mm, . . . ) that can be used for a procedure. The diagnostic imaging device 2 selects a stent that exceeds the lesion length and has the minimum length from among the stent products. The diagnostic imaging device 2 then superimposes and displays the stent region 7 having the length of the selected stent such that both ends of the selected stent are located in the second regions HP1 and HD1. The selection of the stent, the determination of the superimposing position of the stent region 7, and the like may be performed by manual operation by the user.

For example, the diagnostic imaging device 2 superimposes and displays the stent region 7 such that the center position (midpoint) of the lesion region L1 in the axial direction of the blood vessel coincides with the center position of the stent region 7. In this case, as illustrated in FIG. 9, downward arrows are displayed at positions corresponding to both ends of the stent, and bidirectional arrows are displayed at portions exceeding the first region L1. The diagnostic imaging device 2 moves the stent region 7 in accordance with an operation input (for example, mouse operation) by the user, and allows the user to determine the optimum indwelling position of the stent.

In this case, as illustrated in FIG. 9, the diagnostic imaging device 2 preferably displays transverse tomographic images at positions corresponding to both ends of the stent region 7, which helps enable the user to search for the optimum indwelling position of the stent while moving the stent region 7.

Although the stent region 7 is superimposed and displayed on the longitudinal tomographic image 5 in the above description, the diagnostic imaging device 2 may display the stent region 7 at a location other than the longitudinal tomographic image 5 (for example, on the gradation bar 6, inside the gradation bar 6, or the like). As described above, the diagnostic imaging device 2 only needs to be able to display the object simulating the treatment device, and the display position is not limited on the longitudinal tomographic image 5.

Figure 10:
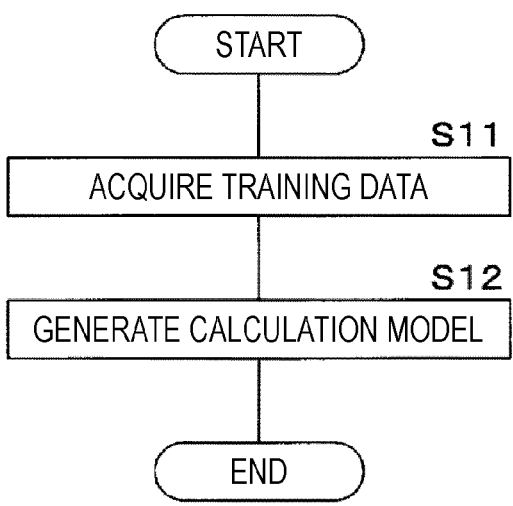
FIG. 10 is a flowchart depicting a procedure of generation processing of a calculation model.

FIG. 10 is a flowchart depicting a procedure of generation processing of the calculation model 51. Processing details for a case where the calculation model 51 is generated by machine learning will be described with reference to FIG. 10.

The control unit 11 of the server 1 acquires training data (second training data) for generating the calculation model 51 (S11). The training data is data in which a correct value of plaque burden is correlated with a transverse tomographic image of a blood vessel for training.

The control unit 11 generates, based on the training data, the calculation model 51 for calculating plaque burden in a case where the transverse tomographic image of the blood vessel is input (S12). Specifically, as described above, the control unit 11 generates a neural network such as a CNN as the calculation model 51. The control unit 11 inputs the blood vessel tomographic image for training to the calculation model 51 to calculate the plaque burden, and compares the plaque burden with the correct value. The control unit 11 optimizes parameters such as weights between neurons so that the plaque burden calculated is approximate to the correct value, and generates the calculation model 51. The control unit 11 ends the series of processing.

Figure 11:
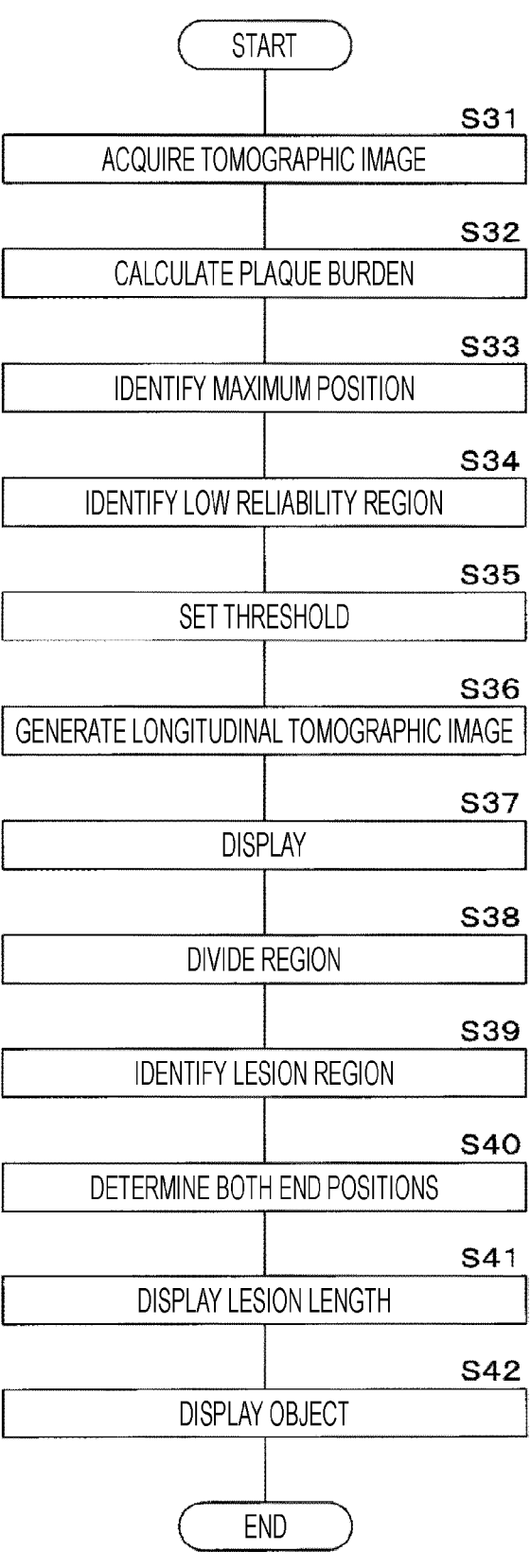
FIG. 11 is a flowchart depicting a procedure of plaque burden calculation processing.

FIG. 11 is a flowchart depicting a procedure of plaque burden calculation processing. Processing details executed by the diagnostic imaging device 2 will be described with reference to FIG. 11.

The control unit 21 of the diagnostic imaging device 2 acquires transverse tomographic images of a plurality of frames obtained by imaging a blood vessel of a patient (S31). The control unit 21 inputs the transverse tomographic image of each frame to the calculation model 51 and calculates the plaque burden in each frame (S32). Specifically, the control unit 21 acquires, from the calculation model 51, the plaque burden in each frame and the reliability of the calculated value.

The control unit 21 identifies a blood vessel position (frame) at which the plaque burden takes the maximum value (S33). The control unit 21 also identifies a low reliability region in which the reliability of the plaque burden is equal to or less than a predetermined value in the axial direction of the blood vessel (S34). Further, the control unit 21 receives a setting input of a threshold (S35). The control unit 21 may skip S35 and set a default threshold.

The control unit 21 generates (reconstructs) a longitudinal tomographic image of the blood vessel on the basis of the transverse tomographic images of the plurality of frames acquired in S31 (S36). The control unit 21 displays the generated longitudinal tomographic image and an object (first object) indicating the magnitude of the plaque burden at each position of the longitudinal tomographic image along the axial direction of the blood vessel (S37). Specifically, as described above, the control unit 21 displays a gradation bar in which the display color is gradually changed according to the magnitude of the plaque burden. In this case, the control unit 21 displays the gradation bar in which the low reliability region is hidden.

The control unit 21 divides, based on the plaque burden at each position (frame) of the blood vessel, the longitudinal tomographic image (longitudinal cross section) of the blood vessel into a first region having the plaque burden equal to or greater than the threshold and a second region having the plaque burden less than the threshold (S38). Specifically, the control unit 21 divides the longitudinal tomographic image into a plurality of regions according to whether or not the plaque burden is equal to or greater than the threshold, and in a case where the length of the low reliability region is equal to or less than a predetermined length, the control unit 21 divides the plurality of first regions or second regions extending over the low reliability region as the same region.

The control unit 21 identifies a first region including the maximum value of the plaque burden as a lesion region (S39). The control unit 21 then determines a region in which both ends of a treatment area to be treated with the treatment device are to be located according to the identified lesion region (S40). Specifically, the control unit 21 determines second regions located on both sides of the lesion region as regions where both ends of the stent indwelled in the blood vessel should be located.

The control unit 21 measures the length in the axial direction of the lesion region identified in S39, that is, the lesion length, and displays the lesion length in correlation with the lesion region in the longitudinal tomographic image (S41). The control unit 21 also displays an object (second object) representing the size of the treatment device in correlation with the longitudinal tomographic image (S42). For example, as described above, the control unit 21 superimposes and displays the stent region representing the length of the stent in the axial direction of the blood vessel on the longitudinal tomographic image such that both ends are located in the region determined in S40. The control unit 21 ends the series of processing.

As described above, according to the first embodiment, the plaque burden at each position of the blood vessel is calculated based on the transverse tomographic images of the plurality of frames obtained by imaging the blood vessel of the patient, and the object such as the gradation bar representing the magnitude of the calculated plaque burden is displayed in correlation with the longitudinal tomographic image, which make it possible to suitably support diagnostic imaging related to vascular treatment such as determination of the indwelling position of the stent.

In addition, according to the first embodiment, the certainty of the calculation result of the plaque burden can be presented to the user by hiding the low reliability region in which the reliability of the calculation result of the plaque burden is relatively low.

Further, according to the first embodiment, it is possible to more suitably support diagnostic imaging by presenting the length of the lesion region (lesion length), the indwelling area of the stent (stent region), and the like.

Further, according to the first embodiment, the longitudinal cross section (longitudinal tomographic image) of the blood vessel is divided into a plurality of regions according to the plaque burden, and regions where both ends of a treatment area of the blood vessel by the treatment device such as the stent are to be located are determined, which make it possible to more suitably support diagnostic imaging related to vascular treatment such as determination of the indwelling position of the stent.

According to the first embodiment, in a case where the length of the low reliability region is equal to or less than the predetermined length, the plurality of regions (first region or second region) extending over the low reliability region is regarded as the same region and divided. As a result, the indwelling position of the stent and the like can be suitably determined while reliability can be ensured.

In the first embodiment, the first region where the plaque burden takes the maximum value is identified as the lesion region. However, the lesion region is not necessary to be a region where the plaque burden takes the maximum value.

Figure 12:
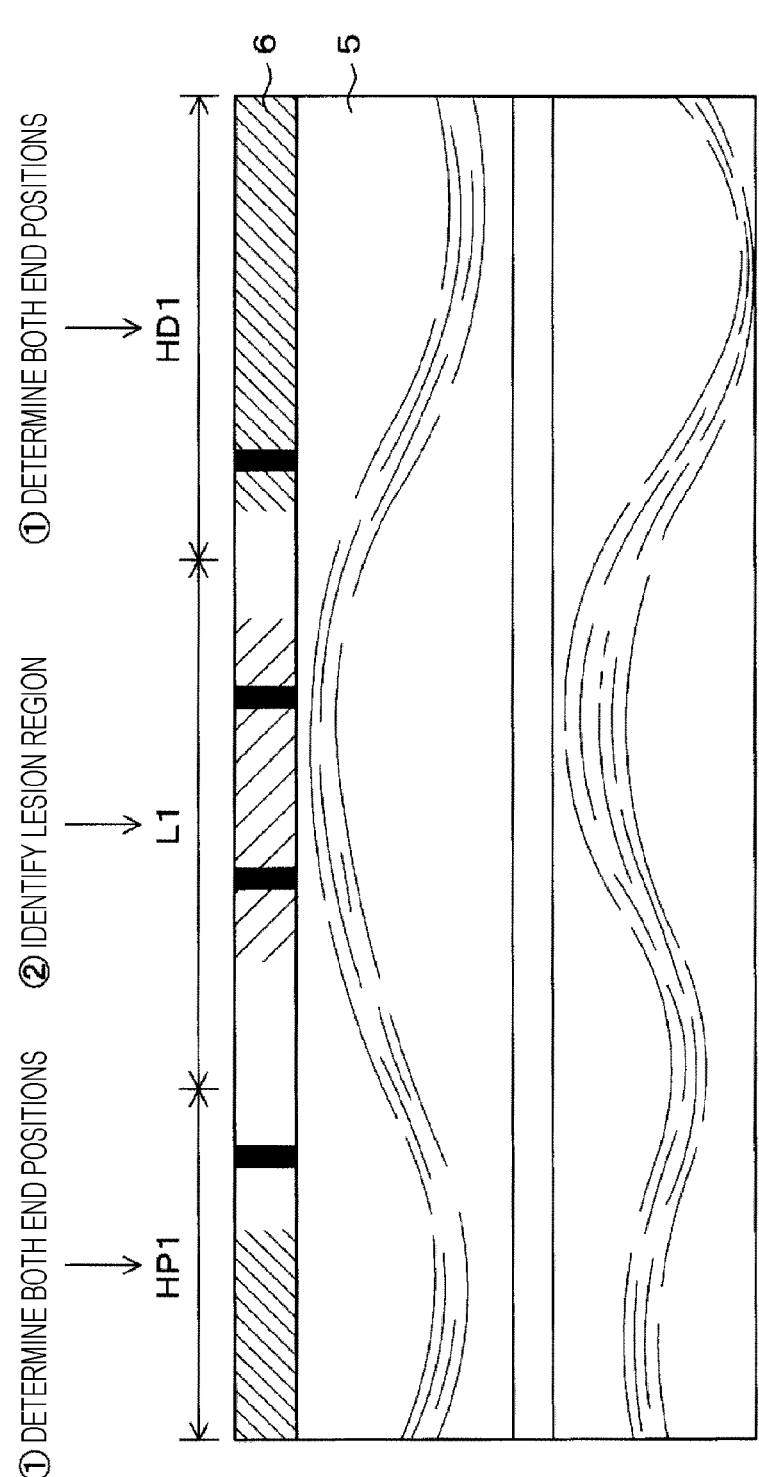
FIG. 12 is an explanatory diagram related to processing for identifying a lesion region according to a first modification.

FIG. 12 is an explanatory diagram related to processing for identifying a lesion region according to the first modification. In the first embodiment, the lesion region is identified first, and then the region where both ends of the stent should be located is determined; however, the region where both ends of the stent should be located may be determined first, and then the lesion region may be identified.

Specifically, after dividing the longitudinal tomographic image 5 into the first regions L1, L2, L3 . . . and the second regions H1, H2, H3 . . . , the diagnostic imaging device 2 searches for two second regions Hy and Hz sandwiching a first region Lx between the two second regions Hy and Hz. In a case where the two second regions Hy and Hz sandwiching the first region Lx are searched, the diagnostic imaging device 2 identifies, as the lesion region Lx, the first region Lx sandwiched between the two second regions Hy and Hz. The diagnostic imaging device 2 then measures the length of the lesion region Lx (lesion length) and superimposes and displays the stent region 7.

As described above, the diagnostic imaging device 2 may determine the region in which the stent is to be indwelled from the positional relationship between the first region and the second region. The determination method described in the first embodiment is an example, and various methods are assumed.

In the first embodiment, the configuration in which the calculation model 51 directly calculates plaque burden has been described. In the present embodiment, description is provided of a configuration in which a plaque region is identified from a blood vessel tomographic image (transverse tomographic image) using another machine learning model to indirectly calculate plaque burden. The same reference numerals are given to the same contents as those of the first embodiment, and the description of the same reference numerals of the first embodiment will be omitted.

Figure 13:
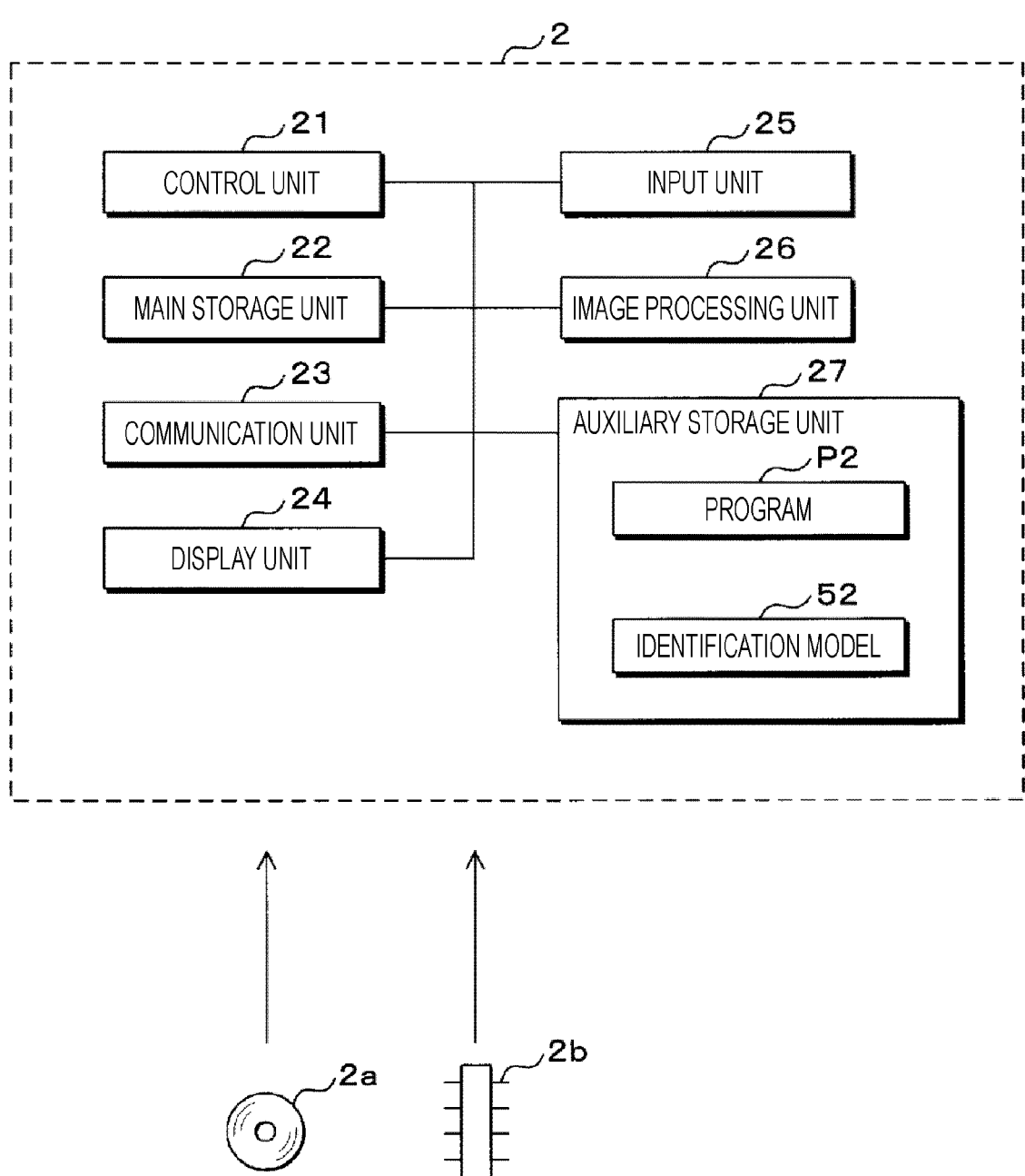
FIG. 13 is a block diagram illustrating a configuration example of a diagnostic imaging device according to a second embodiment.

FIG. 13 is a block diagram illustrating a configuration example of the diagnostic imaging device 2 according to the second embodiment. The auxiliary storage unit 27 of the diagnostic imaging device 2 according to the present embodiment stores an identification model 52. As with the calculation model 51 according to the first embodiment, the identification model 52 is a machine learning model generated by learning predetermined training data, and is a learned model that identifies a plaque region in a blood vessel tomographic image using the blood vessel tomographic image as an input. The identification model 52 is assumed to be used as a program module constituting a part of artificial intelligence software.

Figure 14:
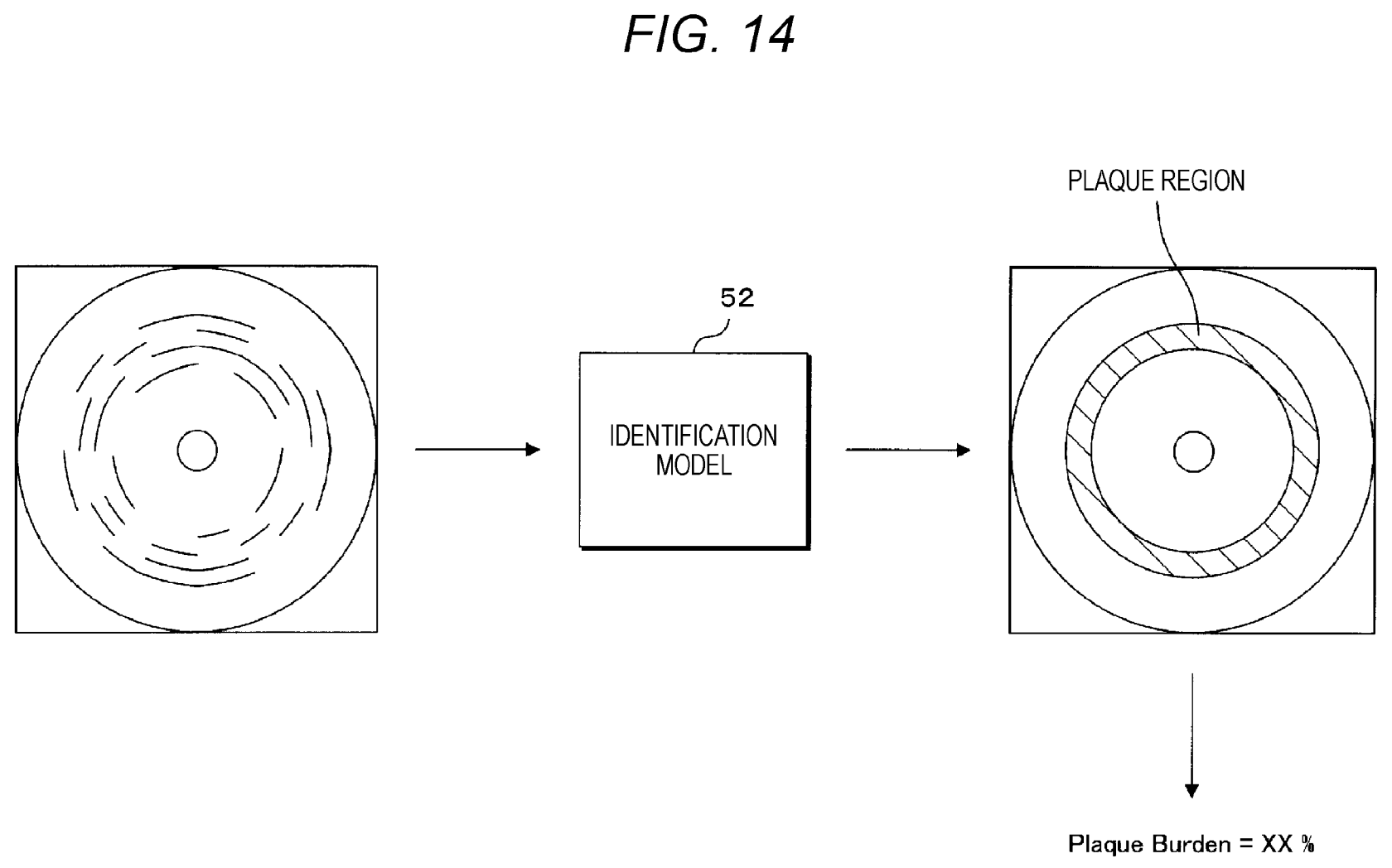

FIG. 14 is an explanatory diagram related to calculation processing of plaque burden according to the second embodiment. FIG. 14 illustrates a state in which an image region (referred to as a "plaque region" in the following description) corresponding to a plaque and a tunica media is identified from a transverse tomographic image of a blood vessel using the identification model 52, and plaque burden is calculated from an area of the identified plaque region. An outline of the present embodiment will be described with reference to FIG. 14.

The identification model 52 is a machine learning model that has learned predetermined training data, and can be, for example, a neural network generated by deep learning. In the present embodiment, the description will be given on the assumption that the identification model 52 is a semantic segmentation model which is a type of CNN.

The semantic segmentation model is a neural network that identifies an object in an image in units of pixels, and includes a convolutional layer (encoder) that convolves an input image and a deconvolutional layer (decoder) that maps a convoluted feature amount to the original image size. In the deconvolutional layer, which object exists at which position in the image is identified based on the feature amount extracted in the convolutional layer, and data obtained by binarizing which object each pixel corresponds to is generated.

The server 1 generates the identification model 52 using training data (first training data) in which data indicating a correct plaque region is correlated with a tomographic image for training. The server 1 inputs the tomographic image for training to the identification model 52 to identify a plaque region, and optimizes parameters such as weights between neurons so that the identified plaque region approximates to the correct plaque region. The diagnostic imaging device 2 identifies a plaque region using the identification model 52 generated by the server 1.

In the present embodiment, the description will be given assuming that the identification model 52 is a semantic segmentation model, but the identification model 52 may be a model based on a neural network other than the semantic segmentation model, a generative adversarial network (GAN), or another learning algorithm.

Alternatively, the server 1 may generate the identification model 52 capable of also identifying a region other than the plaque region by training using training data to which correct answer data on a region other than the plaque region (for example, EEM region, lumen region, and so on) is also given. That is, the identification model 52 only needs to be able to identify at least a plaque region, and may be able to identify other image regions.

In a case where a blood vessel of a patient is imaged, the diagnostic imaging device 2 sequentially inputs tomographic images of frames to the identification model 52, and identifies a plaque region in each frame. The diagnostic imaging device 2 then calculates plaque burden based on the identification result of the plaque region. That is, the diagnostic imaging device 2 calculates the plaque burden by calculating an area of the plaque region and an area of the entire blood vessel including the plaque region.

As described above, the configuration in which the machine learning model directly calculates the plaque burden is not essential, and the plaque burden may be indirectly calculated from a prediction result in the machine learning model.

Figure 15:
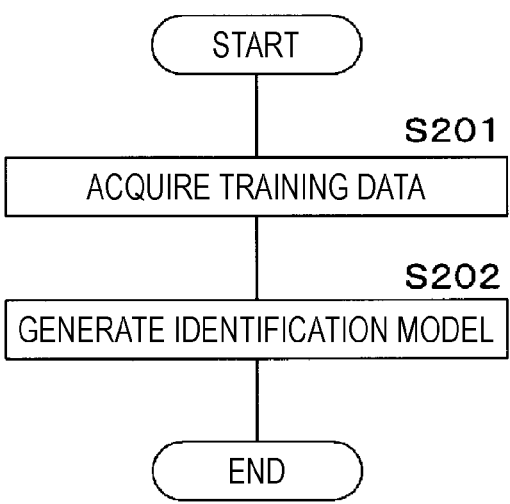
FIG. 15 is a flowchart depicting a procedure of generation processing of an identification model.

FIG. 15 is a flowchart depicting a procedure of generation processing of the identification model 52. Processing details for a case where the identification model 52 is generated by machine learning will be described with reference to FIG. 15.

The control unit 11 of the server 1 acquires training data (first training data) for generating the identification model 52 (S201). The training data is data in which data indicating a correct plaque region is correlated with a transverse tomographic image of a blood vessel for training.

The control unit 11 generates, based on the training data, the identification model 52 for identifying the plaque region in a case where the transverse tomographic image of the blood vessel is input (S202). Specifically, as described above, the control unit 11 generates the CNN related to semantic segmentation as the identification model 52. The control unit 11 inputs a transverse tomographic image for training to the identification model 52 to identify the plaque region, and compares the plaque region with the correct plaque region. The control unit 11 optimizes parameters such as weights between neurons so that the two approximate to each other, and generates the identification model 52. The control unit 11 ends the series of processing.

Figure 16:
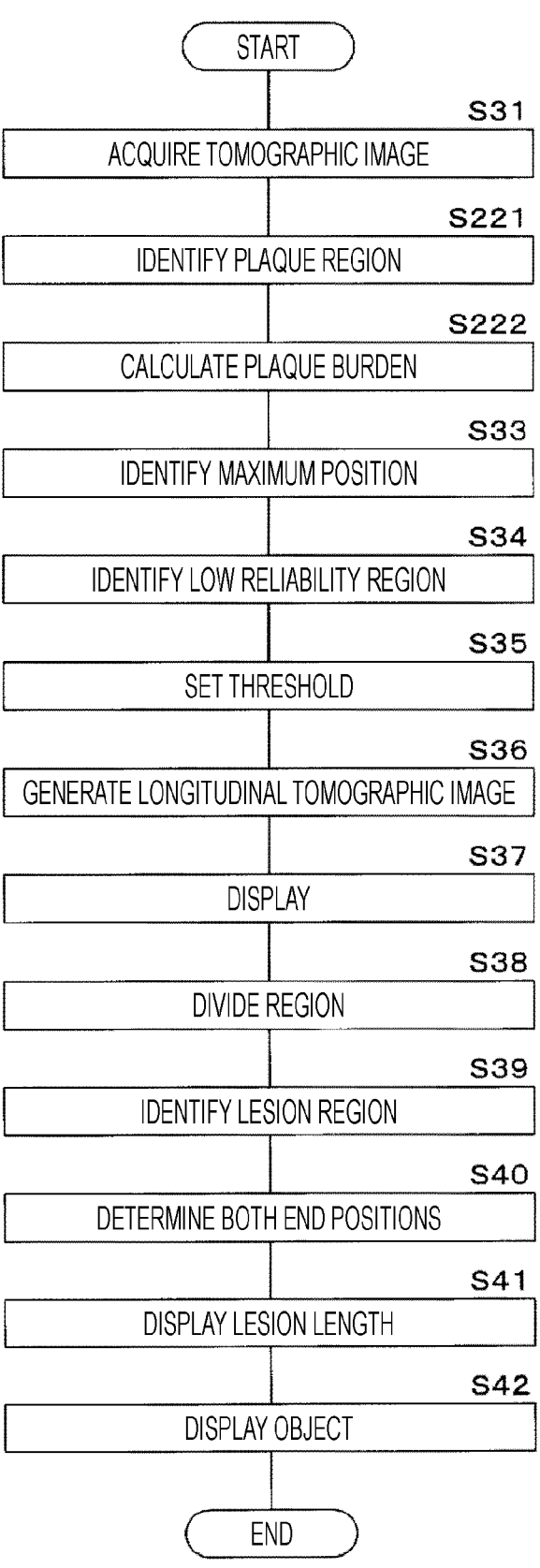
FIG. 16 is a flowchart depicting a procedure of calculation processing of plaque burden according to the second embodiment.

FIG. 16 is a flowchart depicting a procedure of calculation processing of plaque burden according to the second embodiment. After acquiring the transverse tomographic images of the plurality of frames obtained by imaging a blood vessel of a patient (S31), the diagnostic imaging device 2 executes the following processing.

The control unit 21 of the diagnostic imaging device 2 inputs the transverse tomographic image of each frame to the identification model 52 and identifies a plaque region in each frame (S221). The control unit 21 then calculates the plaque burden in each frame on the basis of the identification result (S222). The control unit 21 shifts the processing to S31.

As described above, according to the second embodiment, plaque burden can also be calculated by using the identification result of the identification model 52 that identifies a plaque region from a transverse tomographic image of a blood vessel.

In the second embodiment, the identification model 52 capable of identifying a plaque region in a tomographic image has been described. A parameter such as a weight obtained by learning in the identification model 52 may be applied to the calculation model 51, and transfer learning for generating the calculation model 51 from the learning result in the identification model 52 may be performed.

Figure 17:
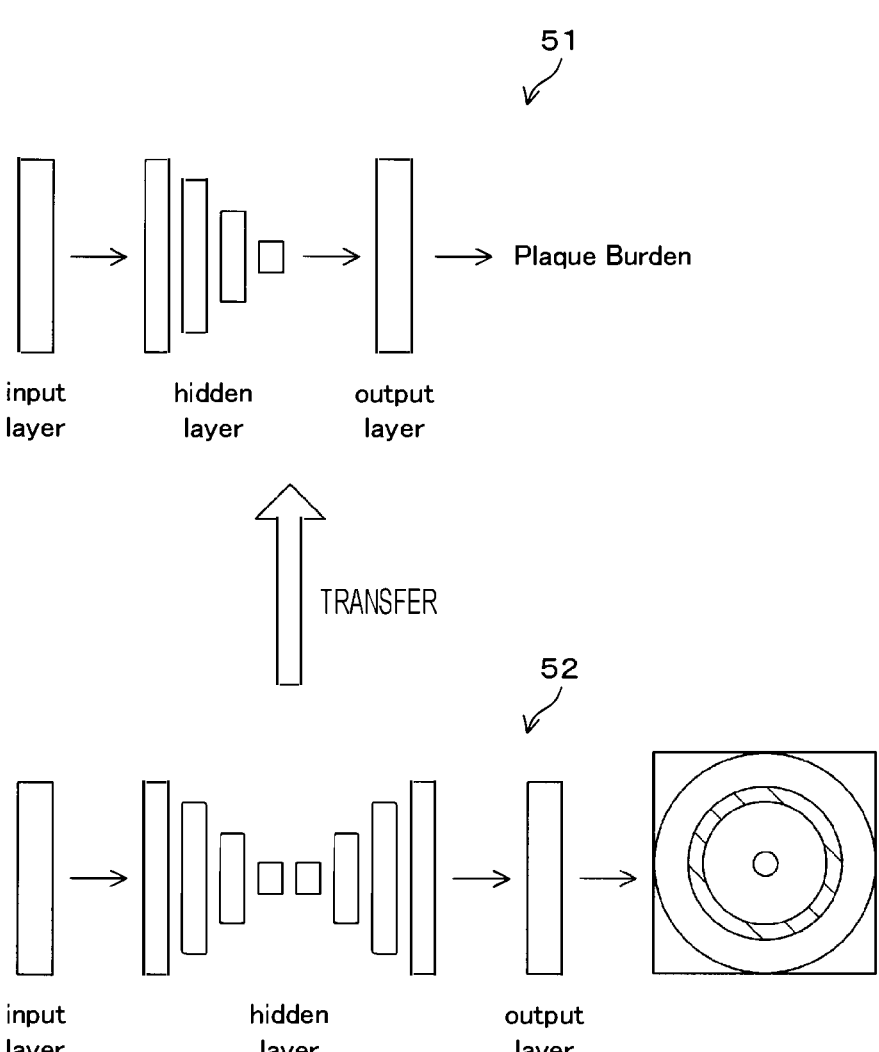
FIG. 17 is an explanatory diagram related to generation processing of a calculation model according to a second modification.

FIG. 17 is an explanatory diagram related to generation processing of the calculation model 51 according to the second modification. FIG. 17 illustrates a state in which some network structures and parameters of the identification model 52 (semantic segmentation model) are applied to the calculation model 51 (CNN) to perform transfer learning. In the present modification, the description is provided assuming that the server 1 has generated the identification model 52.

The server 1 performs learning by setting parameters such as weights obtained by generating (training) the identification model 52 to initial values in the calculation model 51 having a network structure similar to a part of the network structure of the identification model 52. For example, the calculation model 51 has a structure in which an output layer for plaque burden calculation is connected to an input layer similar to the identification model 52 and a part (convolutional layer) of an intermediate layer corresponding to a decoder portion of the identification model 52. The server 1 sets parameters obtained by training the identification model 52 to initial values of the parameters of the intermediate layer, and performs learning by giving training data (first training data). The server 1 inputs the tomographic image for training to calculate the plaque burden, compares the plaque burden with the correct value, and optimizes the parameters so that the two values are approximated. Such transfer learning can reduce the amount of data learned by the calculation model 51 and the learning time of the calculation model 51.

Figure 18:
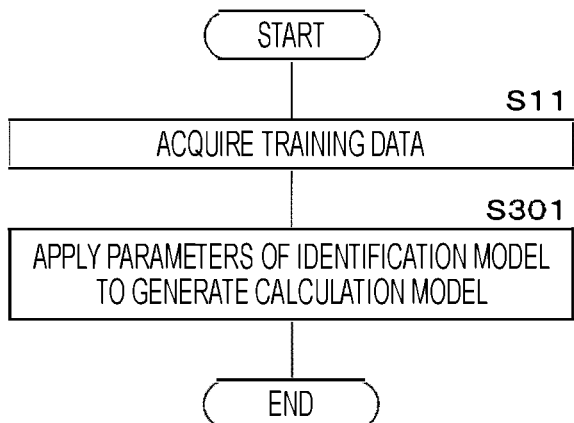
FIG. 18 is a flowchart depicting a procedure of generation processing of a calculation model according to the second modification.

FIG. 18 is a flowchart depicting a procedure of generation processing of the calculation model 51 according to the second modification. After acquiring training data (first training data) for generating the calculation model 51 (S11), the server 1 executes the following processing. The description is provided assuming that the server 1 has generated the identification model 52.

The control unit 11 of the server 1 generates the calculation model 51 based on the parameters obtained by generating the identification model 52 and the training data (S301). Specifically, as described above, the control unit 11 performs learning after setting parameters such as weights obtained by training the identification model 52 to initial values of the parameters of the calculation model 51. The control unit 11 inputs the tomographic image for training to the calculation model 51 to calculate the plaque burden, compares the plaque burden with the correct value, and optimizes the parameters so that the two values are approximated. The control unit 11 ends the series of processing.

As described above, according to the present first modification, the amount of data learned by the calculation model 51 and the learning time of the calculation model 51 can be reduced by using the learning result in the identification model 52.

It is supposed that the embodiments disclosed herein are considered to be an example in all respects and not to be restrictive. The scope of the present invention is indicated not by the above meaning but by the claims and is intended to include all changes within the meaning and scope equivalent to the claims.

The detailed description above describes embodiments of an information processing device, an information processing method, a program, and a model generation method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An information processing device comprising:
a processor and memory operatively connected to the processor, wherein the memory contains instructions that when executed by the processor, causes the processor to:
    acquire transverse tomographic images of a plurality of frames obtained by imaging a blood vessel of a patient;
    calculate plaque burden at each position of the blood vessel along an axial direction of the blood vessel based on the transverse tomographic images of the plurality of frames, the calculated plaque burden being an area ratio of plaque to a transverse cross section of the blood vessel, and is a value obtained by dividing cross-sectional areas of the plaque and a tunica media by a blood vessel cross-sectional area;
    divide a longitudinal cross section of the blood vessel into a first region in which the value of the calculated plaque burden is equal to or greater than a threshold and a second region in which the value of the calculated plaque burden is less than the threshold; and
    determine, in each of the regions obtained by the division, regions in which both ends of a treatment area of the blood vessel with a predetermined treatment device are to be located.

2. The information processing device according to claim 1, wherein the processor is configured to determine regions in which both ends of a stent indwelled in the blood vessel are to be located.

3. The information processing device according to claim 1, wherein the processor is configured to determine two of the second regions sandwiching the first region to be the regions in which the both ends of the stent are to be located.

4. The information processing device according to claim 3, wherein the processor is configured to:
    identify the first region in which the plaque burden takes a maximum value from each of the regions obtained by dividing the longitudinal cross section; and
    determine two of the second regions sandwiching the identified first region to be the regions in which the both ends of the stent are to be located.

5. The information processing device according to claim 1, wherein the processor is configured to:
    receive, from a user, a setting input for setting the threshold; and
    divide the longitudinal cross section according to the set threshold.

6. The information processing device according to claim 1, wherein the processor is configured to:
    calculate the calculated plaque burden in each of the frames by inputting each of the transverse tomographic images of the plurality of frames to a calculation model that has learned to calculate the calculated plaque burden in response to the transverse tomographic image inputted.

7. The information processing device according to claim 1, wherein the processor is configured to:
    identify an image region corresponding to plaque in each of the frames by inputting each of the transverse tomographic images of the plurality of frames to an identification model that has learned to identify the image region in response to the transverse tomographic image inputted; and
    calculate the calculated plaque burden in each of the frames based on an area of the identified image region.

8. The information processing device according to claim 6, wherein the processor is configured to:
    calculate the calculated plaque burden in each of the frames and a reliability indicating certainty of a calculation result of the calculated plaque burden in each of the frames;
    identify a low reliability region in which the reliability is equal to or less than a predetermined value in the longitudinal cross section of the blood vessel; and
    in a case where a length of the low reliability region in the axial direction is equal to or less than a predetermined length, divide the plurality of first regions or second regions extending over the low reliability region as a same region.

9. The information processing device according to claim 8, wherein the processor is configured to:
    receive, from the user, a setting input for setting the predetermined length; and
    divide the longitudinal cross section according to the set predetermined length.

10. The information processing device according to claim 1, further comprising:
    a display unit configured to display a longitudinal tomographic image of the blood vessel corresponding to the longitudinal cross section and a second object that is an object with a predetermined shape displayed in correlation with the longitudinal cross section and has both ends located in the regions in which the both ends of the stent are to be located.

11. The information processing device according to claim 10, wherein the display unit is further configured to display a first object that represents magnitude of the plaque burden at each position of the longitudinal tomographic images along the axial direction.

12. The information processing device according to claim 10,
    wherein the processor is configured to measure a length, in the axial direction, of the first region; and
    the display unit is configured to display the measured length in correlation with the first region in the longitudinal tomographic image.

13. A non-transitory computer-readable medium storing a program, which when executed by a computer, performs processing comprising:
    acquiring transverse tomographic images of a plurality of frames obtained by imaging a blood vessel of a patient;
    calculating plaque burden at each position of the blood vessel along an axial direction of the blood vessel based on the transverse tomographic images of the plurality of frames, the calculated plaque burden being an area ratio of plaque to a transverse cross section of the blood vessel, and is a value obtained by dividing cross-sectional areas of the plaque and a tunica media by a blood vessel cross-sectional area;
    dividing a longitudinal cross section of the blood vessel into a first region in which the value of the calculated plaque burden is equal to or greater than a threshold and a second region in which the value of the calculated plaque burden is less than the threshold; and determining, in each of the regions obtained by the division, regions in which both ends of a treatment area of the blood vessel with a predetermined treatment device are to be located.

14. A model generation method in which a computer executes processing comprising:

acquiring first training data in which data indicating an image region corresponding to plaque is given to a transverse tomographic image obtained by imaging a blood vessel of a patient;

generating, based on the first training data, an identification model for identifying the image region corresponding to the plaque in response to the transverse tomographic image inputted;

acquiring second training data in which a correct value of plaque burden is given to the transverse tomographic image; and generating, based on a learned parameter obtained by generating the identification model and the second training data, a calculation model for calculating the plaque burden in response to the transverse tomographic image inputted, and wherein the calculated plaque burden is an area ratio of plaque to a transverse cross section of the blood vessel, and is a value obtained by dividing cross-sectional areas of the plaque and a tunica media by a blood vessel cross-sectional area.

15. The information processing method according to claim 14, further comprising:

determining regions in which both ends of a stent indwelled in the blood vessel are to be located.

16. The information processing method according to claim 14, further comprising:

determining two of the second regions sandwiching the first region to be the regions in which the both ends of the stent are to be located.

17. The information processing method according to claim 16, further comprising:

identifying the first region in which the plaque burden takes a maximum value from each of the regions obtained by dividing the longitudinal cross section; and determining two of the second regions sandwiching the identified first region to be the regions in which the both ends of the stent are to be located.

18. The information processing method according to claim 14, further comprising:

receiving, from a user, a setting input for setting the threshold; and dividing the longitudinal cross section according to the set threshold.

19. The information processing method according to claim 14, further comprising:

calculating the calculated plaque burden in each of the frames by inputting each of the transverse tomographic images of the plurality of frames to a calculation model that has learned to calculate the calculated plaque burden in response to the transverse tomographic image inputted.

20. The information processing method according to claim 14, further comprising:

identifying an image region corresponding to plaque in each of the frames by inputting each of the transverse tomographic images of the plurality of frames to an identification model that has learned to identify the image region in response to the transverse tomographic image inputted; and calculating the calculated plaque burden in each of the frames based on an area of the identified image region.

* * * * *